United States Patent [19]

Osborne

[11] Patent Number: 4,560,351
[45] Date of Patent: Dec. 24, 1985

[54] METHOD OF AND APPARATUS FOR APPLYING DENTAL TREATMENT FLUID

[76] Inventor: Travis H. Osborne, 905 Lebanon St., Lebanon, Ind. 46052

[21] Appl. No.: 628,141

[22] Filed: Jul. 5, 1984

[51] Int. Cl.$^4$ .............................................. A61C 17/02
[52] U.S. Cl. ........................................ 433/80; 128/66; 604/77; 433/215; 433/216
[58] Field of Search ....................... 433/80, 215, 216; 128/66, 62 A; 604/77

[56] References Cited

U.S. PATENT DOCUMENTS

| | | | |
|---|---|---|---|
| 803,475 | 10/1905 | Dennis | 433/80 |
| 1,934,688 | 11/1933 | Ackerman | 604/77 |
| 2,311,158 | 2/1943 | Conway et al. | 433/36 |
| 2,730,104 | 1/1956 | Newman | 128/66 |
| 3,380,446 | 4/1968 | Martin | 433/216 |
| 3,401,690 | 9/1968 | Martin | 433/216 |
| 3,481,329 | 12/1969 | Warren | 433/216 |
| 3,527,218 | 9/1970 | Westine | 128/62 A |
| 3,731,675 | 5/1973 | Kelly | 128/62 A |

*Primary Examiner*—John J. Wilson
*Attorney, Agent, or Firm*—Woodard, Weikart, Emhardt & Naughton

[57] ABSTRACT

A dental apparatus for applying fluid to the teeth and gums includes as one of its principle components a U-shaped flexible, rubber-like tray having side walls and a bottom wall which define a channel into which the teeth and gums can extend. Attached to the inside perimeter of the side walls near the upper edge of the tray is a flexible, elastic tube. One end of the elastic tube is sealed. The other end of the elastic tube extends through the side wall at the front of the tray and is open for connection to a source of pressurized fluid for inflating the elastic tube. Attached to the bottom wall and communicating with the channel are conduit tubes. A method using the above apparatus to apply a fluid, such as an anesthetic, to the teeth and gums is also disclosed.

11 Claims, 4 Drawing Figures

METHOD OF AND APPARATUS FOR APPLYING DENTAL TREATMENT FLUID

BACKGROUND OF THE INVENTION

1. Field of the Invention

This invention relates in general to a method and apparatus for applying dental treatment fluid, and in particular to a method and apparatus wherein anesthetic or other fluid is applied to the gums by means of a tray which surrounds the teeth and gums.

2. Description of the Prior Art

Dentists normally have their patients on a program whereby their teeth are thoroughly cleaned periodically, such as every six months. If the cleaning process is performed properly, it can be very painful because it is necessary to scrape away foreign material from between the teeth and the gums. Consequently, anesthesia is sometimes applied to the gums, usually by means of hypodermic injection. Such injections of anesthetic are in themselves uncomfortable or painful, as well as being time consuming and not completely effective in anesthetizing the proper portions of the gums.

The method and apparatus of the present invention overcome the above mentioned difficulties, and allow quick, painless and thorough anesthetization of the gums by using a tray shaped to conform to the jaw. The tray has an inflatable seal which seals against the gums so that a vacuum can be applied to suck out saliva from between the teeth and gums. The resultant vacuum in the tray is used to draw a liquid topical anesthetic back into the tray and beneath the gums where the saliva was previously located.

There are several prior known devices and methods for dental treatment which generally include applying a fluid to the teeth and gums by means of a tray, although none of them disclose the present invention. For example, U.S. Pat. Nos. 803,474 and 803,475, both to Dennis and both issued Oct. 31, 1905, show a reservoir shaped to conform to the configuration of the gums and teeth, but there does not appear to be a firm seal between the reservoir and gums. Attached to the reservoir are one or more tubes connected to a compressible bulb which contains the treatment fluid. By alternately compressing and releasing the bulb, the teeth and gums are irrigated with the treatment fluid. The '475 patent mentions that the device may be used as a desensitizer for the gums before mounting crowns and bridges.

Another example of an irrigation type tray is shown in U.S. Pat. No. 1,500,107 to Chandler, issued July 8, 1924. The Chandler device is not designed to seal around the gums.

U.S. Pat. No. 1,371,029 to Jennings, issued March 8, 1921, shows a dental applicator tray having relatively thin and flexible walls for better engaging the teeth and gums, thereby enabling a better vacuum to be formed within the reservoir for drawing impurities or pus from the gums.

Another tray designed to seal against the gums is shown in U.S. Pat. No. 3,380,446 to Martin, issued Apr. 30, 1968. Martin shows a tray which provides a liquid seal at the gums above the line of the teeth. It is mentioned in the patent that it was found necessary to form trays for each person to be treated. In contrast, the inflatable seal of the present invention allows a single tray to be used for a range of different jaw sizes.

U.S. Pat. No. 2,311,158 to Conway et al., issued Feb. 16, 1943, shows a device for making impressions of the gums for the manufacture of dentures. The device has inflatable tubes which apply pressure to a rapidly setting plastic material in directions normal to the anterior and posterior seal areas of the jaw so as to obtain uniform impressions of those areas in the plastic material.

Other patents of general interest are U.S. Pat. Nos. 1,934,688 to Ackerman, issued Nov. 14, 1933; 3,060,935 to Riddell, issued Oct. 30, 1962; 3,481,329 to Warren, issued Dec. 2, 1969; 3,489,141 to Warren, issued Jan. 13, 1970; and 3,772,790 to Swan-Gett et al., issued Nov. 20, 1973.

SUMMARY OF THE INVENTION

A dental apparatus for applyiing fluid to the teeth and gums, according to one embodiment of the present invention, includes a tray for one of the jaws configured to surround the teeth and gums and having a channel into which the teeth and gums can extend. An inflatable seal means is secured to the tray for conforming to the gums and providing an air-tight seal between the channel and the gums. Conduit means are provided for communicating with the channel of the tray.

A method for applying fluid to the teeth and gums utilizing the above apparatus includes the steps of applying the tray to one of the jaws such that the teeth and gums extend into the channel, inflating the inflatable seal means so that an air-tight seal is provided and maintained between the channel and the gums, connecting a vacuum source to the conduit means and drawing out saliva and other fluid from within the channel and introducing a vacuum within the channel, and connecting a source of fluid to be applied to the teeth and gums to the conduit means and allowing the channel vacuum to draw said fluid into the channel.

One object of the present invention is to provide an improved dental apparatus for applying treatment fluid to the teeth and gums which can be manufactured in a few standard sizes to fit the majority of dental patients.

Another object of the present invention is to provide an improved method for applying treatment fluid to the teeth and gums.

Related objects and advantages of the present invention will become apparent from the following description.

DESCRIPTION OF THE PREFERRED EMBODIMENT

Figure 1:
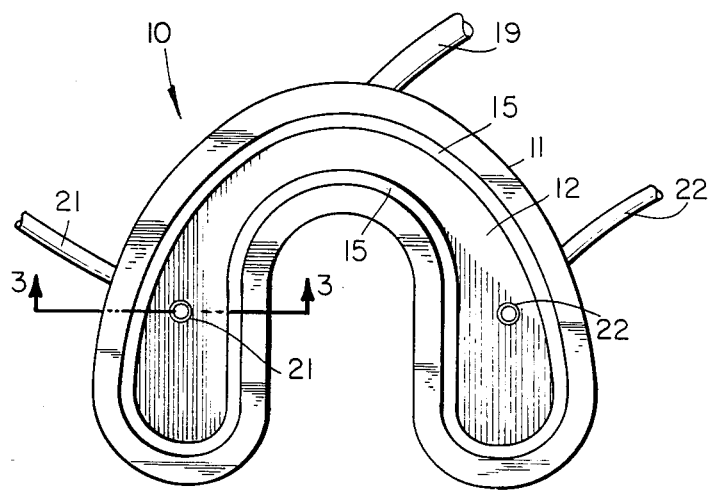
FIG. 1 is a top plan view of the apparatus of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
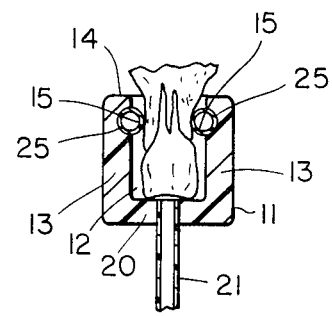
FIG. 3 is a cross sectional view of the apparatus of FIG. 1 taken substantially along the plane 3—3, and showing the teeth and gums in cross section as they would appear when the apparatus is placed on the jaw.
Figure 2:
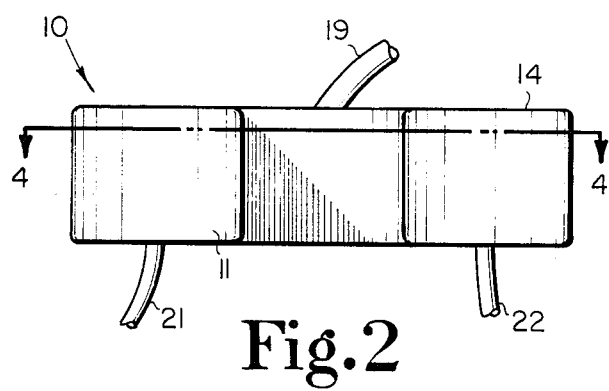
FIG. 2 is a rear elevation view of the apparatus of FIG. 1.
Figure 4:
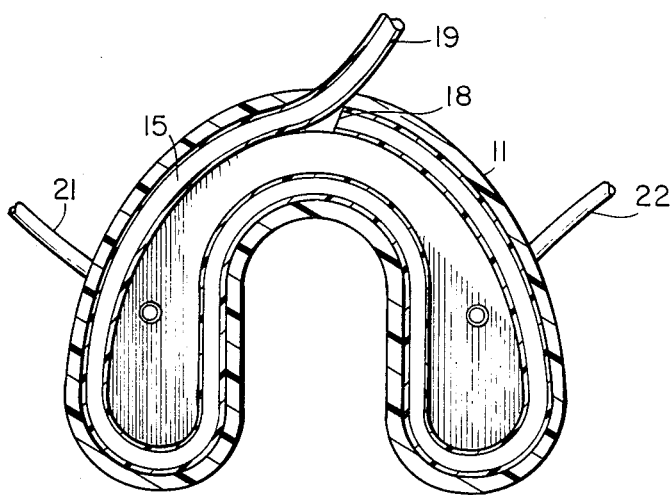
FIG. 4 is a cross sectional view of the apparatus of FIG. 1, taken substantially along a plane 4—4 shown in FIG. 2, and showing in particular the inflatable seal.

Referring to FIGS. 1 through 4, there is illustrated a dental apparatus 10 including as one of its principle components a U-shaped tray 11 having side walls 13 and a bottom wall 20 which define a channel 12 into which the teeth and gums can extend, as shown in FIG. 3. Attached to the inside of side walls 13 near the upper edge 14 of tray 11 is a flexible, elastic tube 15. One end 18 of tube 15 is sealed. The other end 19 of tube 15 extends through side wall 13 at the front of tray 11 and is open for connection to a source of pressurized fluid for inflating tube 15, which will be further described below. Attached to the bottom wall 20 and communicating with channel 12 are tubes 21 and 22.

Tray 11 is molded of food-grade RTV silicone rubber manufactured by General Electric. This material produces a tray which has enough rigidity to hold its shape, yet is flexible enough to be easily inserted into and removed from the mouth. The channel 12 of tray 11 is wider at the rear ends of the tray than at the front of the tray, corresponding to the greater width of the molars as compared to the incisors. Tray 11 has a groove 25 in side walls 13 near the upper edge 14 of tray 11. Groove 25 traverses the full length of the inside perimeter of side walls 13, and is shaped to receive tube 15 therein.

Tube 15 is received within groove 25 and is therefore partially embedded in side walls 13. Silicone rubber adhesive is used to secure tube 15 to tray 11. One end 18 of tube 15 is sealed by the silicone rubber adhesive and the other end 19 is open and extends through side wall 13 at the front of the tray. Tube 15 is made of silicone rubber, is flexible and elastic, and is relatively thin-walled. This allows tube 15 to inflate and expand in diameter when it is pressurized internally by a source of pressurized fluid, such as compressed air, connected to open end 19.

Tubes 21 and 22 are clear plastic tubing of the type commonly used for delivery of intravenous fluid, although any of a variety of plastic or rubber tubing may be used so long as it has sufficient rigidity to resist collapse when a vacuum is applied through the tubing. Tubes 21 and 22 are cemented in place through the bottom wall 20 of tray 11 such that they provide conduits for communicating with channel 12.

Dental apparatus 10 may be used to anesthetize the gums prior to a thorough teeth cleaning, or to apply any other fluid to the teeth and gums, by the following procedure. Tray 11 is applied to the dentition of one of the jaws such that the teeth and gums extend into channel 12 (see FIG. 3). With the teeth firmly seated within the channel, a source of pressurized fluid is connected to end 19 of tube 15 and tube 15 is inflated. As tube 15 inflates and expands, it presses against the gums, conforming to the irregularities in the gums and effecting an air-tight seal between the gums and channel 12 of tray 11. Most dental offices have a source of compressed air available which can be used for this purpose. Alternatively, a large syringe can be connected to end 19 and its plunger depressed to inflate tube 15. After tube 15 is inflated, the source of pressurized fluid can either be left connected to end 19 to maintain tube 15 in its inflated condition, or tube 15 can be closed off by means of a valve or tubing clamp to maintain the inflation, with the pressurized fluid source thereafter being disconnected.

Once the tray is sealed to the gums, a source of vacuum can be connected to one of tubes 21 and 22, with the other tube closed off, and saliva and other fluids can be sucked out from channel 12 and from between the teeth and from between the teeth and the gums. Removal of the saliva prevents dilution of the anesthetic or other fluid which is to be later applied and aids in the penetration of the anesthetic or other fluid beneath the gums, as described below. Because channel 12 is sealed against the gums by tube 15, a vacuum remains within channel 12 after the saliva is removed. The source of vacuum can thereafter be disconnected so long as the tube to which it was connected is first closed off to maintain the vacuum within the channel.

The gums can be anesthetized or otherwise treated by introducing a liquid anesthetic or other fluid into one or both of tubes 21 and 22, although it is advantageous to introduce it into the tube which was not used for drawing out saliva to prevent residual saliva in the tube from being forced back into channel 12. The vacuum in channel 12 will draw the anesthetic or other fluid through the tube 21 or 22 into the channel and into the spaces between the teeth and gums where the saliva was previously located. Because the fluid is drawn beneath the gums by the vacuum, it is possible to insure thorough application of anesthetic to all parts of the gums which may have otherwise been a source of pain when the teeth are cleaned. The anesthetic is left in contact with the gums for a sufficient time to allow the anesthetic action to take place. Thereafter, the anesthetic can be removed from the channel by vacuum suction through tubes 21 and/or 22 in a manner similar to that for removing the saliva. Of course, if the method of the present invention is used to apply a fluid other than an anesthetic to the teeth and/or gums, the precise order and timing of the fluid application and removal steps will be necessarily altered to meet the purposes of the particular treatment.

By deflating tube 15, tray 11 can be removed from the dentition and the cleaning operation or other procedure can be commenced.

There are probably many topical liquid anesthetics which would work well with the apparatus and method of the present invention, although I have found that a viscous fluid anesthetic will deliver through the system better and is easier to use than a thin liquid. I have had satisfactory results with a 2% solution of xylocaine (lidicain HCl) having methyl cellulose added for viscosity, manufactured by the Astra pharmaceutical company, although a 5% solution would probably give longer lasting anesthetic effect. Another anesthetic which can be used is a 20% solution of benzocaine in glycerin.

Because the dental apparatus 10 uses an inflatable seal means (tube 15), it is possible to manufacture the tray 11 in a few standard sizes, with the inflation of the tube 15 being varied to compensate for individual jaw size variations. It is not necessary to manufacture a custom apparatus for most patients, making it practical to use apparatus 10 routinely for anesthetizing the gums of patients prior to teeth cleaning.

It will be appreciated by those familiar with dental practice that the present invention has applications beyond the anesthetization of the gums. There are many situations where it would be desirable to apply a fluid to the teeth and gums such that it penetrates all of the spaces between the teeth and between the teeth and gums, and where it is desirable to keep the tongue and saliva separated from the teeth and gums during treatment. An example would be the application of fluoride to the teeth. Contact between the fluoride solution and all portions of the dentition would be assured, and dilution with saliva would be prevented by use of the apparatus and method of the present invention. Additionally, because the fluoride is kept within a sealed channel about the teeth, the patient would not have to taste it during the treatment period and there would be little possibility of swallowing the treatment fluid.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What I claim is:

1. A dental apparatus for applying fluid to the teeth and gums comprising:

a tray for one of the jaws configured to surround the teeth and gums and having an open topped channel into which the teeth and gums can extend;

inflatable seal means secured to said tray for conforming to the gums and providing an air-tight seal between the gums and the perimeter of the channel; and conduit means for communicating with the channel of said tray.

2. The dental apparatus of claim 1, wherein said tray is constructed of flexible rubber-like material.

3. The dental apparatus of claim 1, wherein said inflatable seal means includes an elastic, flexible thin walled tube.

4. The dental apparatus of claim 3, wherein said inflatable seal means is located proximate the open top of the channel and contacts the gums above the gum-tooth line.

5. The dental apparatus of claim 4, wherein said conduit means includes a tube of sufficient rigidity to resist collapse when a vacuum is applied through said tube.

6. The dental apparatus of claim 5, wherein said conduit means includes separate inlet and outlet tubes.

7. A method for applying fluid to the teeth and gums comprising the steps of:

(a) providing a tray for one of the jaws configured to surround the teeth and gums and having a channel into which the teeth and gums can extend, said tray having inflatable seal means secured thereto for providing an air-tight seal between the gums and the inside perimeter of the channel, said tray having conduit means for communicating with the channel;

(b) applying said tray to one of the jaws such that the teeth and gums extend into the channel;

(c) providing a source of pressurized fluid;

(d) connecting said pressurized fluid source to the inflatable seal means and inflating said inflatable seal means so that an air-tight seal is provided and maintained between said channel and the gums;

(e) providing a source of vacuum;

(f) connecting said vacuum source to said conduit and drawing out saliva and other fluid from within the channel and introducing a vacuum within the channel;

(g) disconnecting said vacuum source from said conduit while maintaining the vacuum within the channel;

(h) providing a source of fluid to be applied to the teeth and gums;

(i) connecting said fluid source to said conduit and allowing said channel vacuum to draw said fluid into said channel.

8. The method of claim 7, wherein the fluid to be applied to the teeth and gums is an anesthetic and including the additional step:

(j) maintaining said fluid in the channel for a therapeutically sufficient length of time.

9. The method of claim 7, wherein the fluid to be applied to the teeth and gums is a preparation for the prevention of tooth decay and including the additional step:

(j) maintaining said fluid in the channel for a therapeutically sufficient length of time.

10. The method of claim 7, wherein the fluid to be applied to the teeth and gums is a medicament for the treatment of tooth or gum disease and including the additional step:

(j) maintaining said fluid in the channel for a therapeutically sufficient length of time.

11. The method of claim 7, wherein said tray is provided with separate conduit means for drawing saliva out of the channel and for drawing the treatment fluid into the channel.

* * * * *